(12) United States Patent
Kim et al.

(10) Patent No.: US 10,392,323 B2
(45) Date of Patent: Aug. 27, 2019

(54) APPARATUS AND METHOD FOR PURIFYING CUMENE

(71) Applicant: LG CHEM, LTD., Seoul (KR)

(72) Inventors: Sung Kyun Kim, Daejeon (KR); Sung Kyu Lee, Daejeon (KR); Joon Ho Shin, Daejeon (KR)

(73) Assignee: LG CHEM, LTD., Seoul (KR)

( * ) Notice: Subject to any disclaimer, the term of this patent is extended or adjusted under 35 U.S.C. 154(b) by 0 days.

(21) Appl. No.: 16/270,393

(22) Filed: Feb. 7, 2019

(65) Prior Publication Data

US 2019/0169094 A1 Jun. 6, 2019

Related U.S. Application Data

(62) Division of application No. 15/107,391, filed as application No. PCT/KR2015/005145 on May 22, 2015.

(30) Foreign Application Priority Data

May 22, 2014 (KR) ........................ 10-2014-0061551

(51) Int. Cl.
| | |
|---|---|
| *C07C 7/04* | (2006.01) |
| *C07C 2/64* | (2006.01) |
| *C07C 7/00* | (2006.01) |
| *B01D 3/00* | (2006.01) |
| *B01D 3/10* | (2006.01) |
| *B01D 3/14* | (2006.01) |
| *B01D 3/42* | (2006.01) |
| *C07C 15/085* | (2006.01) |

(52) U.S. Cl.
CPC ................ *C07C 7/04* (2013.01); *B01D 3/009* (2013.01); *B01D 3/10* (2013.01); *B01D 3/143* (2013.01); *B01D 3/4211* (2013.01); *C07C 2/64* (2013.01); *C07C 7/005* (2013.01); *C07C 15/085* (2013.01); *Y02P 20/124* (2015.11); *Y02P 20/127* (2015.11)

(58) Field of Classification Search
CPC .. C07C 7/005; C07C 7/04; B01D 3/10; B01D 3/143
See application file for complete search history.

(56) References Cited

U.S. PATENT DOCUMENTS

| | | | | |
|---|---|---|---|---|
| 5,003,119 | A | * | 3/1991 | Sardina ................. C07C 2/66 585/323 |
| 5,600,049 | A | | 2/1997 | Sy |

FOREIGN PATENT DOCUMENTS

| | | |
|---|---|---|
| JP | 2012-006947 A | 1/2012 |
| KR | 1020110082160 A | 7/2011 |

(Continued)

OTHER PUBLICATIONS

Riggs, Jim. "Distillation: Major Disturbances and First Level Control," Control Guru Practical Process Control, Apr. 9, 2015, https://controlguru.com/distillation-major-disturbances-first-level-control/.

(Continued)

*Primary Examiner* — Brian A McCaig
(74) *Attorney, Agent, or Firm* — Dentons US LLP

(57) ABSTRACT

The present application relates to an apparatus and method for purifying cumene. The apparatus and method for purifying cumene according to the present application can reduce the amount of energy consumption which occurs during purification processes and can provide an apparatus and method capable of efficiently purifying cumene.

7 Claims, 2 Drawing Sheets

(56) References Cited

FOREIGN PATENT DOCUMENTS

| | | |
|---|---|---|
| KR | 1020120102912 A | 9/2012 |
| KR | 1020130008595 A | 1/2013 |
| KR | 1020130120200 A | 11/2013 |
| WO | 2014003732 A1 | 1/2014 |

OTHER PUBLICATIONS

Norouzi, H.R. et al. (2014) Chemical Engineering Communications, 201, 1270-1293.
Alexandre C. Dimian, et al. Alkylation of Benzene by Propylene to Cumene. Chemical Process Design: Computer-Aided Case Studies. pp. 173-200.

* cited by examiner

[Fig. 1]
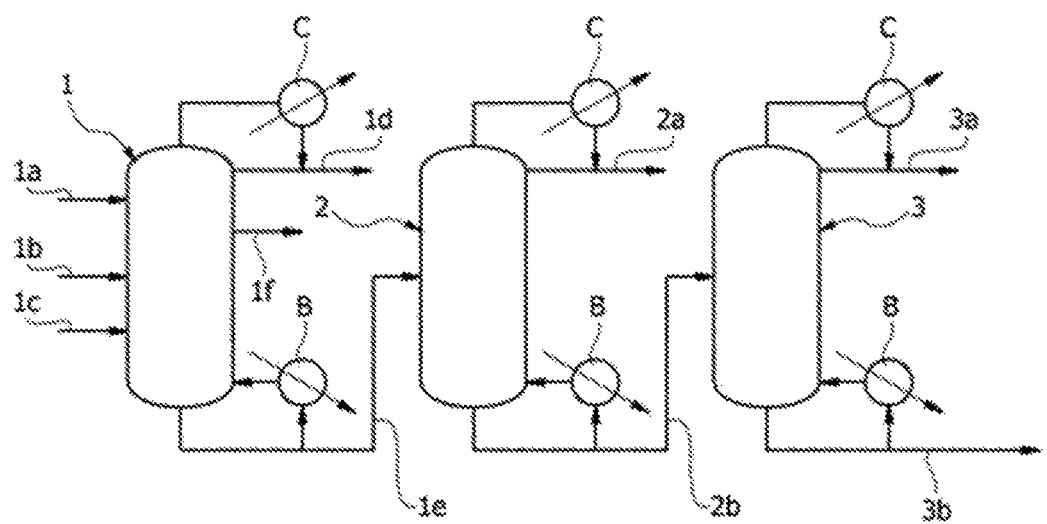
[Fig. 2]
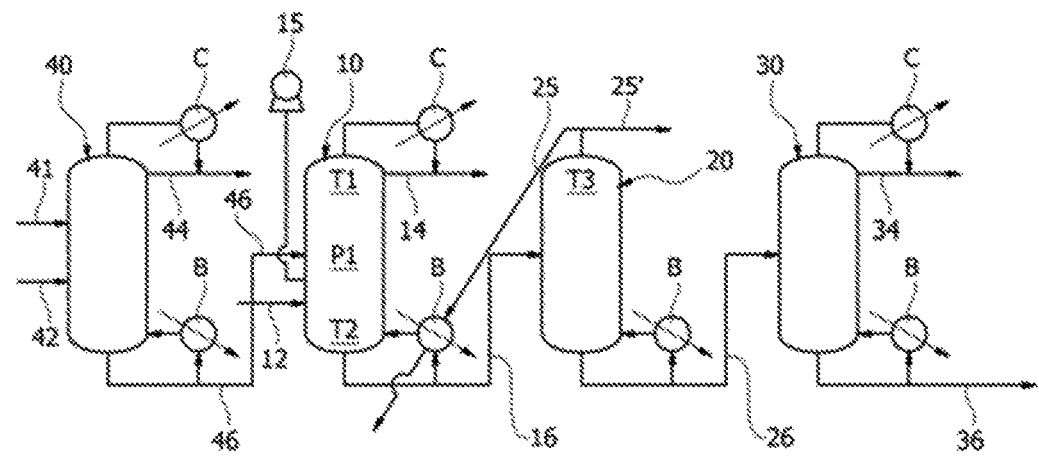

[Fig. 3]
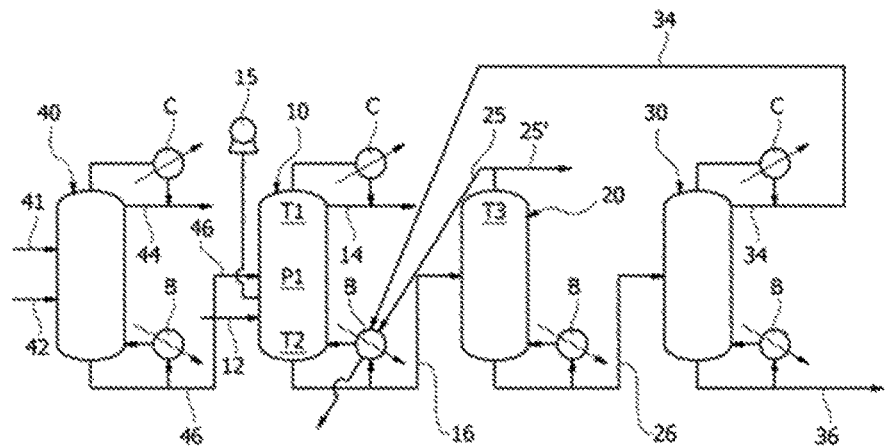
[Fig. 4]
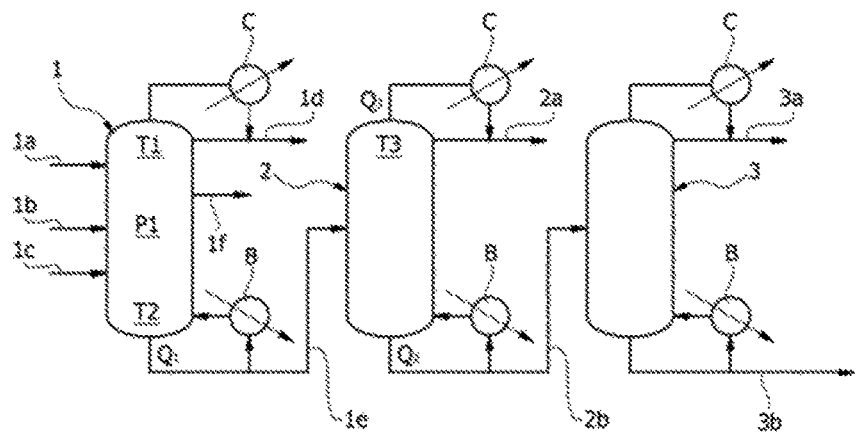
[Fig. 5]
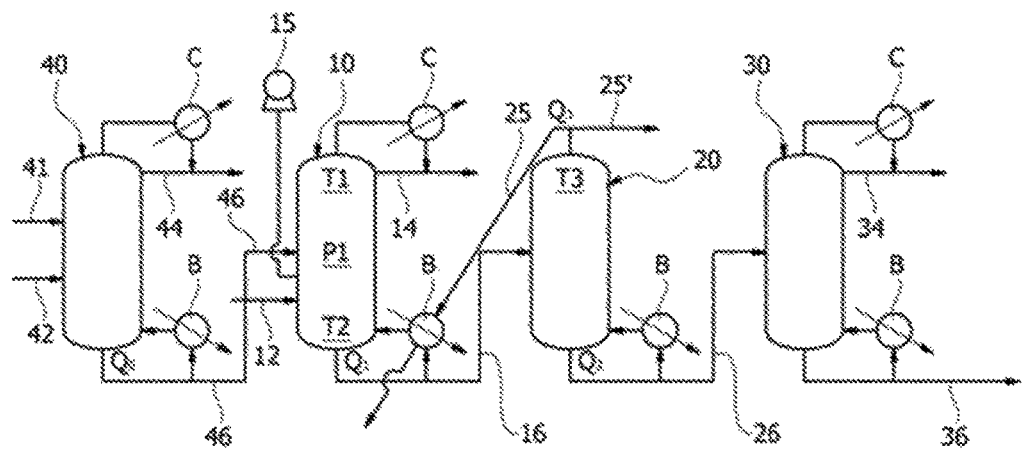

APPARATUS AND METHOD FOR PURIFYING CUMENE

This application is a Divisional of U.S. application Ser. No. 15/107,391, filed Jun. 22, 2016, which is a National Stage Application of International Application No. PCT/KR2015/005145, filed May 22, 2015, and claims the benefit of Korean Patent Application No. 10-2014-0061551, filed May 22, 2014, and the contents of which are incorporated herein by reference in their entirety for all purposes as if fully set forth below.

TECHNICAL FIELD

The present application relates to an apparatus and method for purifying cumene.

Specifically, the present application relates to an apparatus and method for purifying cumene to increase the energy efficiency in the purification process.

BACKGROUND ART

Cumene is isopropylbenzene ($C_6H_5CH(CH_3)_2$), and it is used as an important intermediate material in a variety of chemical industries, polymer industries, etc. At present, most of the cumene (isopropylbenzene) being produced is used for the preparation of phenol, acetone, etc.

Cumene is generally produced by reacting benzene and propylene under liquid or gas phase conditions in the presence of a catalyst. Technologies related to the preparation of cumene are proposed in Korean Unexamined Patent Application Publication No. 10-2011-0082160 and Korean Unexamined Patent Application Publication No. 10-2013-0008595, etc.

Cumene is mostly commercially prepared through an alkylation reaction and a trans alkylation reaction. Accordingly, an apparatus for preparing cumene includes an alkylation reaction unit and a trans alkylation reaction unit.

In the alkylation reaction unit, benzene and propylene react to produce cumene (isopropylbenzene) and, as a by-product, polyisopropylbenzenes (PIPB) such as diisopropylbenzene (DIPB), triisopropylbenzene (TIPB), etc. are produced through a reaction between cumene and propylene. The competitive reaction in the preparation of cumene is a polyalkylation reaction. In other words, it is a side reaction which produces the above-described PIPBs such as DIPB, TIPB, etc.

The trans alkylation reaction unit is used to react polyalkylated benzene, which is the PIPB, etc. produced through the above-described side reaction, with benzene to produce additional cumene.

Also, in addition to the substances described above, light materials (lights) such as C3 (propylene, propane, etc.), etc. and heavy materials (heavies), which are heavier than PIPB, are produced as additional products during the preparation of cumene, and along with these materials, unconsumed benzene, water, etc. are present. Therefore, in the alkylation reaction unit and trans alkylation reaction unit, lights such as C3 (propylene, propane, etc.), etc., PIPB, unconsumed benzene, water and other heavies, etc. are discharged in addition to the cumene (isopropylbenzene) of interest; these materials are either removed or recycled through a purification process in pursuit of high purity cumene.

In general, three distillation columns are used in the purification process of cumene. FIG. 1 is a diagram illustrating the configuration of an apparatus for purifying cumene according to the prior art. Referring to FIG. 1, the purification process for cumene according to the prior art can be schematically illustrated as follows.

The apparatus for purifying cumene is generally installed in connection with the above-described alkylation reaction unit and trans alkylation reaction unit, and includes 3 distillation columns such as a first distillation column, a second distillation column and a third distillation column.

The first distillation column is a benzene column 1 which recovers benzene from streams from the alkylation reaction unit and trans alkylation reaction unit.

In this case, an in-put line 1b which takes in a stream discharged from the alkylation reaction unit and an in-put line 1c which takes in a stream discharged from the trans alkylation reaction unit are connected to the front end portion of the benzene column 1. Also, an in-put line 1a through which fresh benzene flows in is connected to the front end portion of the benzene column 1. In addition, lights such as C3, etc. and water are discharged from the upper portion of the benzene column 1 through a lights out-put line 1d, whereas a cumene stream is discharged from the lower portion through a cumene stream out-put line 1e. Further, benzene is discharged from substantially the center of the benzene column 1 through a benzene recycle line 1f, and the discharged benzene is recycled.

The second distillation column is a cumene column 2 which recovers cumene from the cumene stream discharged from the lower portion of the benzene column 1.

In this case, cumene is discharged from the upper portion of the cumene column 2 through a cumene out-put line 2a and recovered. Also, from the lower portion of the cumene column 2, a PIPB stream is discharged through a PIPB out-put line 2b.

The third distillation column is a PIPB column 3 which takes in and recycles the PIPB stream discharged from the lower portion of the cumene column 2.

In this case, PIPBs such as DIPB, etc. are discharged from the upper portion of the PIPB column 3 through a PIPB out-put line 3a and recycled. Also, from the lower portion of the PIPB column 3, heavies are discharged through a heavies out-put line 3b.

Cumene (isopropylbenzene) of interest can be purified to a high purity and recovered through a purification process such as the above. In addition, energy is consumed in the above-described purification process. To each of the columns 1, 2 and 3, a heat source is provided for the separation of substances by the differences in boiling points, and most of the energy is consumed in such a separation process. In FIG. 1, reference numeral C represents a condenser, and reference numeral B represents a heat exchanger (or reboiler) for supplying heat.

However, the cumene purification process according to the prior art requires a large consumption of energy. As described above, each of the columns 1, 2 and 3 is provided with a heat source for the separation of substances, and without an efficient use of the heat sources being reviewed, the amount of energy consumed is large especially in such a separation process.

DISCLOSURE

Technical Problem

The present application provides an improved apparatus and method for purifying cumene.

With the apparatus and method for purifying cumene according to the present application, excellent energy efficiency can be achieved.

Technical Solution

The present application is devised to solve the aforementioned problems, and relates to an apparatus for purifying cumene including:

a lights cut column which takes in a stream from an alkylation reaction unit and discharges lights and water from the upper portion;

a benzene column which takes in a stream from a trans alkylation reaction unit and the stream discharged through the lower portion of the lights cut column to separate them into benzene and a cumene stream;

a cumene column which takes in the cumene stream from the benzene column to separate it into cumene and a polyisopropylbenzene (PIPB) stream;

a PIPB column which takes in the PIPB stream from the cumene column to separate it into PIPB and heavies;

a temperature dropping unit which reduces the temperature at the lower portion of the benzene column; and a cumene out-put line which is installed at the upper portion of the cumene column.

In the apparatus for purifying cumene according to the present application, the cumene out-put line may be connected to a heat exchanger of the benzene column to supply heat to the lower portion of the benzene column.

In one example, the benzene column and cumene column may operate in the ways to satisfy Mathematical Formula 1 below.

$$T_3-T_2 \geq 10° C. \qquad \text{[Mathematical Formula 1]}$$

(In the Mathematical Formula 1 above, $T_2$ represents the temperature at the lower portion of the benzene column, whereas $T_3$ represents the temperature at the upper portion of the cumene column).

In one example, the PIPB column may include a PIPB out-put line installed at the upper portion, and the PIPB out-put line may be connected to one or more heat exchangers selected among a heat exchanger of the benzene column and a heat exchanger of the cumene column.

In addition, the present application may relate to a method for purifying cumene, where the method includes:

a lights removal process in which a stream from the alkylation reaction unit is introduced into the lights cut column and removed of lights and water;

a benzene separation process in which a stream from the trans alkylation reaction unit and the stream discharged through the lower portion of the lights cut column are introduced into the benzene column and separated into benzene and a cumene stream;

a cumene separation process in which the cumene stream separated earlier is introduced into the cumene column and separated into cumene and a PIPB stream; and a PIPB separation process in which the PIPB stream separated earlier is introduced into the PIPB column and separated into PIPB and heavies.

In one example, the method for purifying cumene according to the present application may further include a process in which the cumene discharged at the upper portion of the cumene column passes through the heat exchanger of the benzene column.

In one example, the method for purifying cumene according to the present application may have the temperature at the lower portion of the benzene column maintained in the range of 130° C. to 200° C.

In one example, the method for purifying cumene according to the present application may have the temperature at the upper portion of the cumene column maintained in the range of 140° C. to 210° C.

In one example, the method for purifying cumene according to the present application may be operated in the way that the benzene column and cumene column satisfy Mathematical Formula 1 below.

$$T_3-T_2 \geq 10° C. \qquad \text{[Mathematical Formula 1]}$$

(In the Mathematical Formula 1 above, $T_2$ represents the temperature at the lower portion of the benzene column, whereas $T_3$ represents the temperature at the upper portion of the cumene column).

In one example, the method for purifying cumene according to the present application may have the pressure in the benzene column maintained in the range of 10 to 230 kPa.

Advantageous Effects

According to the present application, the purification process is improved so that the energy efficiency can increase. Specifically, according to the present application, the vapor heat source of the cumene column is used as the heat source for the benzene column, and therefore, the amount of energy consumed can be effectively reduced.

DESCRIPTION OF DRAWINGS

FIG. 1 is a diagram illustrating the configuration of an apparatus for purifying cumene according to the prior art.

FIG. 2 is a diagram illustrating the configuration of an apparatus for purifying cumene according to the first embodiment of the present application.

FIG. 3 is a diagram illustrating the configuration of an apparatus for purifying cumene according to the second embodiment of the present application.

FIG. 4 is a diagram illustrating the configuration of an apparatus for purifying cumene applied in a comparative example.

FIG. 5 is a diagram illustrating the configuration of an apparatus for purifying cumene applied in an example.

DESCRIPTION OF REFERENCE NUMERALS

10: benzene column
12: in-put line for stream from trans alkylation reaction unit
14: benzene recycle line
15: temperature dropping unit
16: cumene stream out-put line
20: cumene column
25: cumene out-put line
26: polyisopropylbenzene (PIPB) stream out-put line
30: PIPB column
34: PIPB out-put line
36: heavies out-put line
40: lights cut column
41: benzene in-put line
42: in-put line for stream from alkylation reaction unit
44: upper stream out-put line
46: lower stream out-put line

MODES FOR INVENTION

Hereinafter, the apparatus and method for purifying cumene according to the present application will be described in more detail with reference to the accompanying drawings and an example.

In the present specification, "and/or" is used to indicate that one or more of the components listed before or after are included.

In the present specification, "connection", "installation", "combination", etc. refer to the two members which can be engaged with or disengaged from each other, as well as to an integral structure. Specifically, the terms such as "connection", "installation", "combination", etc. describe, for example, two members which are configured to be engaged with or disengaged from each other through a force-fit manner, a fitting manner using grooves and projections, a coupling manner using coupling members such as screws, bolts, pieces, rivets, brackets, etc., as well as an integral body of two members which become inseparable once combined through welding, an adhesive, an integral molding or the like.

The terms such as "first", "second", "third", "one end", "the other end", etc. in the present specification are used to distinguish one element from the other, and it should be understood that each of the components is not limited by the above-described terms. Hereinafter, in the description of the present application, detailed descriptions of any related generic functions or configurations well-known in the art will be omitted.

In the present application, an "A stream" refers to a stream which includes at least an 'A' component, and it may include the 'A' component as a main component. For example, a "polyisopropylbenzene (PIPB) stream" is a stream which includes at least 'PIPB', and it may include 'PIPB' as a main component.

Meanwhile, the above-described 'including PIPB as a main component' may mean that PIPB is included the most among various components of the stream.

In the present application, an "A/B stream" refers to a stream which includes at least an 'A' component and a 'B' component, and an "A/B/C stream" refers to a stream which includes at least an 'A' component, an 'B' component and a 'C' component. For example, "benzene/cumene/PIPB stream" may refer to a stream which includes at least 'benzene', 'cumene' and 'PIPB'.

In the present application, an "A column" refers to a column which separates at least an 'A' substance from an inflow. For example, "a benzene column 10" is a column which separates at least 'benzene', and "a cumene column 20" is a column which separates at least 'cumene'. Also, "a PIPB column 30" is a column which separates at least 'PIPB'.

The present application relates to an apparatus for purifying cumene. The apparatus for purifying cumene according to the present application may be installed in connection with, for example, a preparation apparatus of cumene.

In one example, the apparatus for purifying cumene according to the present application may be installed in connection with the alkylation reaction unit and trans alkylation reaction unit which constitute the preparation apparatus of cumene.

As described earlier, in the above-described alkylation reaction unit, benzene and propylene react to produce PIPBs such as DIPB, TIPB, etc.

In this case, the produced cumene is separated and recovered through a recovery line, and the stream including the above-described by-product is discharged through a separate line.

In addition to the above-described PIPB as a by-product, lights such as C3 (propylene, propane, etc.), etc., unrecovered cumene in a small amount, unconsumed benzene, water, other high-weight heavies, etc. are present in the stream discharged from the above-described alkylation reaction unit.

In addition, in the above-described trans alkylation reaction unit, polyalkylated benzene, which is the PIPB produced through the above-described side reaction, reacts with benzene to produce additional cumene. In the stream discharged from the above-described trans alkylation reaction unit, heavies which are heavier than PIPB are present in addition to PIPB.

The apparatus for purifying cumene according to the present application can take in a stream from the alkylation reaction unit and a stream from the trans alkylation reaction unit, and purify them as described above. In this case, there is no particular limitation to the above-described streams, as long as they are discharged from the alkylation reaction unit and trans alkylation reaction unit. For example, the stream discharged from the above-described alkylation reaction unit may be a by-product stream from which cumene is removed (recovered) by separation, or in some cases, it may be a cumene stream which is separated through a cumene recovery line.

Specifically, the apparatus for purifying cumene according to the present application may take in a stream from the alkylation reaction unit and a stream from the trans alkylation reaction unit separately through distillation columns, which are different from each other.

In one example, the apparatus for purifying cumene according to the present application includes, as exemplified in FIG. 2, a lights cut column 40 which is installed in front of a benzene column 10; the benzene column 10 which takes in a lower stream from the lights cut column 40 and separates it into benzene and a cumene stream; a cumene column 20 which takes in the cumene stream from the benzene column 10 and separates it into cumene and a PIPB stream; a PIPB column 30 which takes in the PIPB stream from the cumene column 20 and separates it into PIPB and heavies; a temperature dropping unit 15 which reduces the temperature at the lower portion of the benzene column 10; and a cumene out-put line 25 which is installed at the upper portion of the cumene column 20. In this case, the cumene out-put line 25 may be connected to a heat exchanger B of the benzene column 10 to supply heat to the lower portion of the benzene column 10.

In a specific example, the lights cut column 40 can take in a stream from the alkylation reaction unit to remove lights and water by discharging them from the upper portion.

In a specific example, the benzene column 10 can serve to take in a stream discharged from the lower portion of the lights cut column 40 and a stream from the trans alkylation reaction unit to separate them into benzene and a cumene stream.

In a specific example, the cumene column 20 can serve to take in the cumene stream from the benzene column 10 to separate it into cumene and a PIPB stream.

In a specific example, the PIPB column 30 can serve to take in the PIPB stream from the cumene column 20 to separate it into PIPB and heavies.

Hereinafter, the apparatus for purifying cumene according to the present application will be described in more detail with reference to accompanying drawings.

FIG. 2 is an exemplifying diagram of the apparatus for purifying cumene according to the present application.

Referring to FIG. 2, the apparatus for purifying cumene according to the present application includes a benzene column 10, a cumene column 20 which is installed at the back of the benzene column 10, a PIPB column 30 which is installed at the back of the cumene column 20, and a lights cut column 40 which is installed in front of the benzene column 10.

In the present application, each of the columns 10, 20, 30 and 40 may be selected from the distillation columns used in distillation processes in general industries.

In addition, there is no particular limitation to the operating conditions, for example, the plate number, inner diameter, pressure, temperature, reflux ratio of the upper and lower effluents, etc. of each of the columns 10, 20, 30 and 40 in the present application, and they may be freely redesigned by an ordinary person skilled in the art within a range in which the objects of the present application can be achieved.

As shown in FIG. 2, a condenser and/or heat exchanger (or reboiler) may be installed in each of the columns 10, 20, 30 and 40 of the present application. In FIG. 2, reference numeral C represents a condenser, whereas reference numeral B represents a heat exchanger (or reboiler).

In this case, the condenser C and/or heat exchanger B may be installed or not installed depending on each of the columns 10, 20, 30 and 40.

In this case, the condenser C and heat exchanger B are, unless specified otherwise, the components which may be omitted even when illustrated in a diagram, or, conversely, they are the components which may be included (installed) even when not illustrated in a diagram.

The apparatus for purifying cumene according to the present application has a structure which, compared to the conventional purification apparatus as illustrated in FIG. 1, further includes a light cut column 40. As changes are made to the influent and effluent flow lines accordingly, a structure with improved energy efficiency can be obtained.

Specifically, the lights cut column 40 of the apparatus for purifying cumene according to the present application can remove lights and water by taking in a stream of the alkylation reaction unit and discharging from the upper portion.

The lights cut column 40 may include at least one of in-put lines 41 and 42 installed in the front end portion.

In one example, the in-put lines 41 and 42 may include an in-put line 42 through which a stream discharged in the alkylation reaction unit flows in.

In addition, in another exemplary embodiment, the in-put lines 41 and 42 may further include a benzene in-put line 41 through which fresh benzene flows in. That is, the lights cut column 40 is positioned in the front end in the apparatus for purifying cumene according to the present application, and may further include a benzene in-put line through which fresh benzene flows in.

As illustrated in FIG. 2, the benzene in-put line 41 may be installed at substantially the upper portion of the lights cut column 40, and an in-put line 42 for a stream from the alkylation reaction unit may be installed below the benzene in-put line 41, but they are not limited thereto.

The lights cut column 40 takes in fresh benzene and a stream from the alkylation reaction unit, and separates them into an upper stream (materials having a low boiling point) and a lower stream (materials having a high boiling point). The lights cut column 40 includes an upper stream out-put line 44 installed at the upper portion and a lower stream out-put line 46 installed at the lower portion.

Through the upper stream out-put line 44, lights such as C3 (propylene, propane, etc.), etc. and water are discharged to be removed. In this case, the above-described lights such as C3 (propylene, propane, etc.), etc. may be included mainly in a stream from the alkylation reaction unit and the above-described water may be included mainly in fresh benzene. In addition, the above-described lower stream contains materials with a high boiling point which are inclusive of benzene, cumene, PIPB, heavies, etc. and exclusive of lights and water. Such a lower stream is discharged through the lower stream out-put line 46 and introduced into the benzene column 10.

The benzene column 10 is installed at the back of the lights cut column 40, and it may separate the introduced stream into benzene and a cumene stream.

The benzene column 10 may have an in-put line 12 for a stream from the trans alkylation reaction unit and a lower stream out-put line 46 of the lights cut column 40 connected to its front end. Accordingly, the benzene column 10 may take in the stream from the trans alkylation reaction unit and a stream discharged through the lower portion of the lights cut column 40 to separate them into benzene and a cumene stream.

In addition, the benzene column 10 may include a benzene recycle line 14 installed at the upper portion and a cumene stream out-put line 16 installed at the lower portion.

In the benzene column 10, separation into 2 phases of benzene and a cumene stream is possible, and the benzene separated in the benzene column 10 can be discharged through the benzene recycle line 14 and recycled.

In this case, the benzene discharged through the benzene recycle line 14 can be, for example, supplied to the alkylation reaction unit and/or trans alkylation reaction unit and recycled, and, in some cases, recycled through the benzene in-put line 41 into the lights cut column 40.

The above-described cumene stream may be discharged, for example, through the cumene stream out-put line 16 and introduced into the cumene column 20.

The cumene column 20 takes in the cumene stream from the benzene column 10 and separates it into cumene and a PIPB stream. The cumene column 20 may include a cumene out-put line 25 installed at the upper portion and a PIPB stream out-put line 26 installed at the lower portion.

The cumene separated at the cumene column 20 may be discharged from the upper portion through the cumene out-put line 25, and the discharged cumene may be recovered as a product.

In this case, one end of the cumene out-put line 25 is connected to the upper portion of the cumene column 20 and the other end is connected to a heat exchanger B of the benzene column 10 to provide a heat source to the benzene column 10.

In one example, the cumene out-put line may be connected to a heat exchanger of the benzene column to supply heat to the lower portion of the benzene column. As above, when the cumene out-put line is connected to the heat exchanger of the benzene column, the vapor of cumene becomes a heat source, and therefore, the energy required for supplying heat to the lower portion of the benzene column can be reduced. More specific details will be described below.

In addition, the PIPB stream separated in the cumene column 20 is discharged through the out-put line 26 and introduced into the PIPB column 30.

The PIPB column 30 can take in the PIPB stream from the cumene column 20 and separate it into PIPB and heavies.

In this case, according to one embodiment, the PIPB column 30 may include a PIPB out-put line 34 installed at the upper portion and a heavies out-put line 36 installed at the lower portion.

The PIPB separated in the above-described PIPB column 30 is discharged from the upper portion through the out-put line 34, and the discharged PIPB may be supplied, for example, to the trans alkylation reaction unit and recycled.

The PIPB stream introduced from the cumene column 20 may contain PIPBs such as DIPB, TIPB, etc.

In this case, for example, DIPB among the above-described DIPB and TIPB may be separated through the PIPB column 30, discharged through the out-put line 34, supplied to the trans alkylation reaction unit and recycled.

In addition, the PIPB column 30 may include, for example, a plurality of PIPB out-put lines 34 which separate PIPBs by type.

Specifically, the PIPB column 30 includes a TIPB out-put line installed at a plate having substantially a median plate number and a DIPB out-put line 34 installed at the upper portion, and thus, it can separate polyalkylation benzene by type at multiple plates.

Meanwhile, the heavies discharged through the heavies out-put line 36 are the heaviest materials in the process, and may specifically refer to materials heavier (materials having a higher boiling point) than PIPB.

Such heavies may be discharged through the out-put line 36, cooled and then sent to a storage tank.

The apparatus for purifying cumene according to the present application includes 4 columns 10, 20, 30 and 40 as described above, and, additionally as the means to improve energy efficiency, it may include a temperature dropping unit 15 which drops a temperature $T_2$ at the lower portion of the benzene column 10.

In the present application, there is no particular limitation to the temperature dropping unit 15 as long as it can reduce the temperature $T_2$ at the lower portion of the benzene column 10.

According to an exemplary embodiment of the present application, such a dropping of temperature may be achieved by reducing the internal pressure $P_1$ of the benzene column 10.

For example, the temperature dropping unit 15 may include a pressure dropping means to reduce the internal pressure of the benzene column 10.

Specifically, the temperature dropping unit 15 may include a vacuum pump as the pressure dropping means. In the drawings, a vacuum pump is illustrated as an example of the temperature dropping unit 15. However, in the present application, the temperature dropping unit 15 is not limited to a vacuum pump, and it is not particularly limited to a certain type as long as it can reduce the temperature $T_2$ at the lower portion of the benzene column 10.

In addition, there is no particular limitation to the installation position of the temperature dropping unit 15. The temperature dropping unit 15 may be installed inside the benzene column 10, or it may be installed in a way so that it is positioned outside the benzene column 10 and connected to the benzene column 10.

The temperature dropping unit (e.g. a vacuum pump is used) 15 may be installed in a way so that it is connected to a side wall of the benzene column 10.

In this case, the vacuum pump may be connected and installed as close as possible to the side wall of the benzene column 10, so that it can result in a maximum ability to reduce pressure (suction strength).

In dropping of the temperature $T_2$ at the lower portion of the benzene column 10, the temperature $T_2$ at the lower portion should be maintained higher than the temperature $T_1$ at the upper portion so as not to adversely affect the separation efficiency of the benzene column 10.

In other words, $T_2$ should be maintained higher than $T_1$ as illustrated in FIG. 2. In consideration of this point, it may be preferable that the temperature $T_2$ at the lower portion is reduced as a result of a reduced internal pressure $P_1$ as exemplified above.

Specifically, when the internal pressure $P_1$ is reduced, the temperature $T_1$ at the upper portion and temperature $T_2$ at the lower portion drop in even proportions, and therefore, $T_2 > T_1$ can be maintained with a simple operation.

The apparatus for purifying cumene according to the present application includes a cumene out-put line installed at the upper portion of the cumene column. The cumene out-put line 25 may be connected to a heat exchanger B of the benzene column 10 to supply heat to the lower portion of the benzene column 10.

Specifically, a heat exchanger B is installed at the lower portion of the benzene column 10, and the cumene out-put line 25 may be connected to such a heat exchanger B. In other words, one end of the cumene out-put line 25 may be connected to the upper portion of the cumene column 20, whereas the other end may be connected to the heat exchanger B of the benzene column 10.

More specifically, when the purification apparatus is designed as described above, it may be able to supply heat to the lower portion of the benzene column 10 by reducing the temperature $T_2$ at the lower portion of the benzene column 10 and passing the cumene, which is discharged from the upper portion of the cumene column 20, through the heat exchanger B of the benzene column 10 prior to recovery. In addition, the cumene which passed through the heat exchanger B may be recovered as a product.

Therefore, according to the present application, the vapor heat source of the cumene discharged from the cumene column 20 may be used as a replacement for the source of heat supplied to the lower portion of the benzene column 10. Therefore, the energy required for supplying heat to the lower portion of the benzene column 10 can be reduced.

In addition, the temperature $T_2$ at the lower portion of the benzene column 10 has been reduced earlier as described above, and therefore, the heat required for the separation process in the benzene column 10 can be sufficiently provided by the vapor heat source of cumene alone, and this may be efficient in recycling heat energy.

In one example, the benzene column 10 and cumene column 20 may be operated in the way that Mathematical Formula 1 below is satisfied.

$$T_3 - T_2 > 10° C. \qquad \text{[Mathematical Formula 1]}$$

In the Mathematical Formula above, $T_2$ represents the temperature at the lower portion on the inside of the benzene column 10, whereas $T_3$ represents the temperature at the upper portion of the inside of the cumene column 20.

In other words, operations may be performed in the way that the temperature $T_3$ at the upper portion of the inside of the cumene column 20 is maintained higher than the temperature $T_2$ at the lower portion of the inside of the benzene column 10 by 10° C. or more.

When the Mathematical Formula 1 above is satisfied, it may be highly beneficial in terms of energy efficiency. That is, when the Mathematical Formula 1 above is satisfied, the amount of energy consumed can be effectively reduced.

Considering this point, it may be preferable to have the temperature $T_3$ at the upper portion of the cumene column 20 maintained higher than the temperature $T_2$ at the lower portion of the benzene column 10 by 15° C. or more ($T_3 - T_2 > 15°$ C.), or 20° C. or more ($T_3 - T_2 > 20°$ C.), by reducing the temperature $T_2$ at the lower portion.

In this case, there is no particular upper limit to the difference between the two temperatures, but it may be, for example, 80° C. or 60° C. In other words, $T_3-T_2>80°$ C. or $T_3-T_2>60°$ C. may be satisfied.

In one example, the temperature $T_3$ at the upper portion of the cumene column 20 may be 140° C. or more, and specifically, it may be in the range of 140° C. to 210° C.

The temperature $T_2$ at the lower portion of the benzene column 10 may be, for example, in the range of 200° C. or less, and specifically, 130° C. to 200° C., through a dropping of the internal pressure $P_1$.

In addition, the internal pressure $P_1$ of the benzene column 10 may be beneficial to the process when maintained at a low level.

The internal pressure $P_1$ of the benzene column 10 can have, for example, the temperature $T_2$ at the lower portion maintained within the above-described range, through a pressure dropping.

Specifically, the internal pressure $P_1$ of the benzene column 10 may be maintained at the level of, for example, 500 kPa or less, 300 kPa or less, or 230 kPa or less. At the same time, the lower limit of the internal pressure $P_1$ of the benzene column 10 may be 5 kPa or more, or 10 kPa or more, but it is not particularly limited thereto. The internal pressure $P_1$ of the benzene column 10 may be adjusted to fall within the range of, for example, 5 kPa to 300 kPa, 5 kPa to 300 kPa, 10 kPa to 300 kPa, or 10 kPa to 230 kPa.

Meanwhile, in the present application, the separation of cumene in the cumene column 20 may include the case where all of the cumene passes through the heat exchanger B of the benzene column 10 and the case where a part of the cumene passes through the heat exchanger B of the benzene column 10.

Specifically, the cumene separated in the cumene column 20 may be supplied in its entirety through the cumene out-put line 25 to the heat exchanger B of the benzene column 10. In addition, the cumene separated in the cumene column 20 is discharged through two lines 25 and 25'; a part of it may be supplied through a first cumene out-put line 25 to the heat exchanger B of the benzene column 10, while the rest being discharged through a second cumene recovery line 25'.

In this case, the cumene discharged through the second cumene recovery line 25' is cooled and then collected in a storage tank. At the same time, the cumene which is supplied through the first cumene out-put line 25 to the heat exchanger B of the benzene column 10 may be cooled after providing heat to the benzene column 10 and then collected in a storage tank.

In addition, according to an exemplary embodiment, the cumene out-put line 25 may be heat-insulated.

Specifically, the cumene out-put line 25 may have a covering of a thermal insulation material or heating means such as hot wires on the surface so that it can avoid heat loss during the course of cumene transport through the cumene out-put line 25 to the heat exchanger B of the benzene column 10.

With the apparatus for purifying cumene according to the present application, lights and water are removed in advance by the lights cut column 40 before they are introduced into the benzene column 10; therefore, an adverse effect which may result from a temperature dropping of the benzene column 10 can be prevented, and at the same time, a purification process in the benzene column 10 can be improved and energy efficiency can be ultimately enhanced.

Specifically, when it is intended to remove lights such as C3 (propylene, propane, etc.), etc. (included in alkylation reactants) and water (included in fresh benzene) from the benzene column 10 in a conventional way of discharging them from the upper portion without requiring installation of the lights cut column 40, a temperature dropping of the benzene column 10 may cause much stress to the condenser C.

More specifically, in the reduction of the temperature $T_2$ at the lower portion of the benzene column 10, to reduce the internal pressure $P_1$ of the benzene column 10 as described earlier may be considered as a preferable option. In this case, when the internal pressure $P_1$ of the benzene column 10 drops, the temperature $T_1$ at the upper portion as well as the temperature $T_2$ at the lower portion decreases. In this case, the temperature $T_1$ at the upper portion may decrease below zero due to an excessive reduction in the internal pressure $P_1$, causing much stress to the condenser C.

However, the apparatus for purifying cumene according to the present application has a lights cut column 40 installed in front of the benzene column 10 as described above; in this way, it can remove lights in alkylation reactants and water (moisture) in fresh benzene through the lights cut column 40 in advance, thereby preventing the above-described phenomenon and enabling a temperature dropping through the reduction of pressure $P_1$ of the benzene column 10. In addition, from the upper portion of the benzene column 10, substantially pure benzene can be separated.

In addition, according to the prior art, lights and water (from the upper portion of a benzene column 1), benzene (from the central portion of the benzene column 1) and a cumene stream (from the upper portion of the benzene column 1) are separately discharged from the apparatus for purifying cumene as seen in FIG. 1. In this case, sectioning is required to accommodate the 3 phases, and therefore, operating conditions (plate number, pressure, temperature, etc.) of the benzene column 1 may be difficult to deal with, and the separation efficiency of benzene may degrade. In other words, it may be difficult to separate benzene with a high purity.

In contrast, with the apparatus for purifying cumene according to embodiments of the present application, lights and water are removed by the lights cut column 40 in advance as shown in FIG. 2. Therefore, a separation process into 2 phases of benzene and a cumene stream takes place in the benzene column 10, and, accordingly, setting up the operation conditions for the upper portion and lower portion may be made easier. In addition, with only the operation conditions for benzene (pressure, temperature, etc.) being considered, high purity benzene can be obtained by separation at a high efficiency.

Moreover, with the apparatus for purifying cumene according to the present application, the purification process can be further improved by connecting the in-put line 42 for a stream from the alkylation reaction unit to the lights cut column 40, and connecting the in-put line 12 for a stream from the trans alkylation reaction unit to the benzene column 10 as described earlier.

For example, connecting both stream in-put lines 12 and 42 to the lights cut column 40 may be taken into consideration; but in this case, a load may be exerted on the lights cut column 40, thus reducing efficiency in the separation process in the lights cut column 40 itself and, furthermore, in carrying out the overall purification process continuously.

However, in the apparatus for purifying cumene according to the present application, each of 2 streams is separately introduced into the lights cut column 40 and benzene column 10, respectively, thereby reducing the load on each of columns 10 and 40 and enabling a continuous purification process with high efficiency.

Also, the apparatus for purifying cumene according to the present application can supply heat to the lower portion of any one or both of the benzene column 10 and cumene column 20 by passing the PIPB discharged at the upper portion of the PIPB column 30 through one or more heat exchangers B selected among the heat exchanger B of the benzene column 10 and heat exchanger B of the cumene column 20.

Specifically, the PIPB out-put line 34 may be connected to one or more heat exchangers B selected among the heat exchanger B of the benzene column 10 and heat exchanger B of the cumene column 20. Accordingly, the vapor heat source of PIPB may be recycled as the heat source of the benzene column 10 and/or of the cumene column 20, and thus, energy efficiency can increase.

More specifically, as illustrated in FIG. 3, the PIPB out-put line 34 may be connected, for example, to the heat exchanger B of the benzene column 10. In addition, the PIPB which passed through a heat exchanger B may be supplied to the trans alkylation reaction unit after supplying heat to be recycled.

The present application is also related to a method for purifying cumene using the above-described apparatus. The method for purifying cumene according to the present application may be carried out by using the above-described lights cut column, benzene column, cumene column and PIPB column.

For example, the method for purifying cumene according to the present application includes:

a lights removal process in which a stream from the alkylation reaction unit is introduced into the lights cut column and removed of lights and water;

a benzene separation process in which a stream from the trans alkylation reaction unit and the stream discharged through the lower portion of the lights cut column are introduced into the benzene column and separated into benzene and a cumene stream;

a cumene separation process in which the cumene stream separated earlier is introduced into the cumene column and separated into cumene and a PIPB stream; and a PIPB separation process in which the PIPB stream separated earlier is introduced into the PIPB column and separated into PIPB and heavies.

The above-described lights removal process may be carried out in the lights cut column 40. A stream from the alkylation reaction unit is introduced into the lights cut column 40, and, for example, lights and water may be removed through the upper portion, and materials having a high boiling point, specifically, benzene, cumene, PIPB, heavies, etc. may be separated through the lower portion.

Also, the lights removal process may further include a step of taking in benzene through the benzene in-put line installed at the front end portion.

The above-described benzene separation process may be carried out in the benzene column 10, and it may include a step of taking in a stream from the trans alkylation reaction unit and a stream discharged at the lower portion of the lights cut column to separate, for example, benzene through the upper portion and a cumene stream through the lower portion.

The benzene separated through the upper portion may be supplied through a benzene recycle line to, for example, the alkylation reaction unit and/or trans alkylation reaction unit and recycled, and in some cases, it may be recycled through the benzene in-put line 41 to the lights cut column 40.

The above-described benzene column may include a temperature dropping unit 15 which drops the temperature $T_2$ at the lower portion, and it may be possible that the decrease in the temperature of the benzene column is induced from the reduction of the internal pressure of the benzene column.

In other words, the method for purifying cumene according to the present application can induce dropping of the internal pressure of the benzene column, ultimately reducing the temperature at the lower portion of the benzene column, by further including a lights removal process prior to the benzene separation process.

In addition, as the temperature at the lower portion of the benzene column drops, the vapor heat source of cumene, which may be obtained by passing the cumene discharged at the upper portion of the cumene column through the heat exchanger of the benzene column, can single-handedly supply enough heat required for the separation process of the benzene column 10, ultimately leading to energy savings.

In one example, the method for purifying cumene according to the present application may include having the internal pressure of the benzene column maintained in the range of 10 kPa to 230 kPa. In addition, it may include having the temperature at the lower portion of the benzene column maintained in the range of 130° C. to 200° C.

The above-described cumene separation process may be carried out in the cumene column 20, and it may include steps of taking in a cumene stream and separating, for example, cumene through the upper portion and a PIPB stream through the lower portion.

The cumene separated through the upper portion earlier may be passed through, for example, the heat exchanger of the benzene column.

In other words, the method for purifying cumene according to the present application may further include a step of passing the cumene discharged from the upper portion of the cumene column through the heat exchanger of the benzene column. When the cumene separated from the cumene column is passed through the heat exchanger of the benzene column as described above, the cumene vapor becomes the heat source, and thus, the energy of the heat exchanger installed in the benzene column can be reduced.

In one example, the method for purifying cumene according to the present application may include having the temperature at the upper portion of the cumene column maintained in the range of 140° C. to 210° C.

In addition, the method for purifying cumene according to the present application may include operating the benzene column 10 and cumene column 20 in a way so that Mathematical Formula 1 below is satisfied.

$$T_3 - T_2 > 10° \text{ C.} \quad \text{[Mathematical Formula 1]}$$

In the Mathematical Formula above, $T_2$ represents the temperature at the lower portion of the inside of the benzene column 10, whereas $T_3$ represents the temperature at the upper portion of the inside of the cumene column 20.

In other words, operations may be performed in a way so that the temperature $T_3$ at the upper portion of the inside of the cumene column 20 is maintained higher than the temperature $T_2$ at the lower portion of the inside of the benzene column 10 by 10° C. or more.

When the Mathematical Formula 1 above is satisfied, it may be highly beneficial in terms of energy efficiency. That is, when Mathematical Formula 1 above is satisfied, the amount of energy consumed can be effectively reduced.

Also, the method for purifying cumene according to the present application may further include a step of passing the PIPB discharged from the upper portion of the PIPB column through one or more heat exchangers selected among the heat exchanger of the benzene column and heat exchanger of the cumene column.

Specifically, by connecting the PIPB out-put line 34 to one or more heat exchangers B selected among the heat exchanger B of the benzene column 10 and heat exchanger B of the cumene column 20, the above-described PIPB may be passed through any one or more heat exchangers selected among the heat exchanger of the benzene column and heat exchanger of the cumene column. Accordingly, the vapor heat source of PIPB can be recycled into the heat source of the benzene column 10 and/or cumene column 20, thus increasing the energy efficiency.

Hereinafter, an example of the present application and a comparative example will be provided. The example below is provided merely to help understanding of the present application, and it should not be understood as limiting the technical scope of the present application.

Example 1

Cumene was purified using an apparatus as shown in FIG. 5. The apparatus shown in FIG. 5 is identical to the apparatus shown in FIG. 2, but in FIG. 5, Q was specified for the description of the heat energy consumed in each of columns 10, 20 and 40.

Referring to FIG. 5, fresh benzene 41 and a stream 42 which was discharged from the alkylation reaction unit were introduced through each of in-put lines 41 and 42 into the lights cut column 40.

Lights and water were removed through an upper out-put line 44, whereas a lower stream was introduced through a lower out-put line 46 into the benzene column 10.

As for the benzene column 10, the lower stream 46 from the lights cut column 40 was introduced through the in-put line 12 along with a stream 12 discharged from the trans alkylation reaction unit. Also, benzene was discharged from the upper portion through the out-put line 14 to be recycled into the lights cut column 40, whereas a cumene stream was discharged from the lower portion through the out-put line 16 and introduced into the cumene column 20.

In addition, in the cumene column 20, cumene was discharged from the upper portion through the out-put line 25, but it was passed through the heat exchanger B of the benzene column 10 for heat supply. The PIPB stream discharged from the lower portion through the out-put line 26 was introduced into the PIPB column 30. In addition, in the PIPB column 30, PIPB was discharged from the upper portion through the out-put line 34 to be recycled into the trans alkylation unit, and heavies were discharged from the lower portion through the out-put line 36 and cooled.

To carry out the purification process according to this example, a dropping of the internal pressure $P_1$ of the benzene column 10 was induced. In this case, the internal pressure $P_1$ of the benzene column 10 was reduced by a vacuum pump 15 installed at one end of the benzene column 10 and maintained at about 35 kPa. The temperature $T_1$ at the upper portion and temperature $T_2$ at the lower portion of the benzene column 10 were maintained at about 50° C. and about 150° C., respectively, through a dropping of the internal pressure $P_1$. Also, the temperature $T_3$ at the upper portion of the cumene column 20 was maintained at about 160° C. Here, each of the temperatures $T_1$ and $T_3$ at the upper portions is an averaged temperature at the upper portion of each column, whereas the temperature $T_2$ at the lower portion is an averaged temperature of the lower portion of a column. In addition, the heat energy $Q_0$ supplied to the lights cut column 40, heat energy $Q_1$ supplied to the benzene column 10, heat energy $Q_2$ supplied to the cumene column 20 and heat energy $Q_3$ discharged from the upper portion of the cumene column 20 were measured. The measurements are shown in Table 1 below.

Comparative Example

Cumene was purified using an apparatus as shown in FIG. 4. The apparatus shown in FIG. 4 is identical to the apparatus shown in FIG. 1, but in FIG. 4, Q was specified for the description of the heat energy consumed in each of columns 1 and 2. The comparative example is a conventional general process, and description of the specific process well-known in the art will be omitted.

Referring to FIG. 4, fresh benzene 1a, a stream 1b discharged from an alkylation reaction unit and a stream 1c discharged from a trans alkylation reaction unit were introduced to a benzene column 1 respectively through each of in-put lines 1a, 1b and 1c. Also, discharges of lights and water through an upper out-put line 1d, benzene through a central out-put line if and a cumene stream through a lower out-put line 1e were carried out.

In addition, cumene was discharged through an out-put line 2a at the upper portion of a cumene column 2 to be recovered, and a PIPB stream discharged through an out-put line 2b at the lower portion was introduced to a PIPB column 3. Also, PIPB was discharged through an out-put line 3a at the upper portion of a PIPB column 3 to be recycled into a trans alkylation reaction unit, and heavies were discharged through an out-put line 3d at the lower portion and cooled.

In the purification process as the above, the internal pressure $P_1$ of the benzene column 1 was maintained at about 310 kPa, and the temperature $T_1$ at the upper portion and temperature $T_2$ at the lower portion of the benzene column 1 were maintained at about 50° C. and about 215° C., respectively. Also, the temperature $T_3$ at the upper portion of the cumene column 2 was maintained at about 160° C. Here, each of the temperatures $T_1$ and $T_3$ at upper portions is an averaged temperature at the upper portion of each column, whereas the temperature $T_2$ at the lower portion is an averaged temperature of the lower portion of a column. In addition, the heat energy $Q_1$ supplied to the benzene column 1, heat energy $Q_2$ supplied to the cumene column 2 and heat energy $Q_3$ discharged from the upper portion of the cumene column 2 were measured. The measurements are shown in Table 1 below.

TABLE 1

<Results of heat energy evaluation>

| Note | P1 (kPa) | $T_3$-$T_2$ | $Q_0$ | $Q_1$ | $Q_2$ | $Q_3$ | $Q_T$ | Amount saved (ΔQ) |
|---|---|---|---|---|---|---|---|---|
| Comparative Example | 310 | −55° C. | — | 8.4 | 5.2 | 6.1 | 13.6 | — |
| Example | 35 | 10° C. | 0.95 | 6.94 | 7.6 | 6.1 | 9.39 | 4.21 |

P1: internal pressure of benzene column (kPa)
$Q_0$: heat energy supplied to lights cut column (Gcal/hr)
$Q_1$: heat energy supplied to benzene column (Gcal/hr)
$Q_2$: heat energy supplied to cumene column (Gcal/hr)
$Q_3$: heat energy of cumene discharged from cumene column (Gcal/hr)
$Q_T$: sum of heat energy actually used in purification process (Gcal/hr)
$T_3$: temperature at upper portion of cumene column
$T_2$: temperature at lower portion of benzene column As shown in Table 1 above, it can be seen that, when a dropping of the temperature $T_2$ at the lower portion is induced and the vapor heat source $Q_3$ of cumene is supplemented as the heat source $Q_1$ of the benzene column 10 through a dropping of internal pressure $P_1$ of the benzene column 10 according to Example of the present application, heat energy of 4.21 Gcal/hr can be saved (saved by about 31%).

In this case, the heat energy $Q_1$ supplied to the benzene column 10 is 6.94 Gcal/hr, but the heat energy $Q_3$ of cumene at 6.1 Gcal/hr is supplied to the benzene column 10, and thus, the heat energy $Q_1$ $Q_3$ actually used in the benzene column 10 is 0.84 Gcal/hr. The heat energy $Q_T$ actually used in the purification process is 9.36 Gcal/hr in the case of the example, indicating that significant amount of energy is saved as compared to 13.6 Gcal/hr in the case of the comparative example.

The invention claimed is:

1. A method for purifying cumene, the method comprising:
    a light material removal process in which a stream from an alkylation reaction unit is introduced to a lights cut column to be removed of lights and water, wherein the lights cut column includes a first output stream and a second output stream, wherein the first output stream discharges lights and water and is located at a higher position than the second output stream;
    a benzene separation process in which a stream from a transalkylation reaction unit and the second output stream of the lights cut column are introduced to a benzene column to be separated into a benzene stream and a first cumene stream, wherein the benzene stream is located at a higher position than the first cumene stream;
    a cumene separation process in which the first cumene stream is introduced to a cumene column to be separated into a second cumene stream and a first polyisopropylbenzene stream, wherein the second cumene stream is located at a higher position than the first polyisopropylbenzene stream;
    a polyisopropylbenzene separation process in which the first polyisopropylbenzene stream is introduced to a polyisopropyl column to be separated into a second polyisopropylbenzene stream and a heavy materials stream; and
    a process of passing the second cumene stream discharged from the cumene column through a heat exchanger of the benzene column.

2. The method of claim 1, wherein the light material removal process further includes introduction of benzene to the lights cut column through a benzene input line.

3. The method of claim 1, wherein a temperature of the benzene column at a discharge position of the first cumene stream is maintained in a range of 130° C. to 200° C.

4. The method of claim 1, wherein a temperature of the cumene column at a discharge position of the second cumene stream is maintained in a range of 140° C. to 210° C.

5. The method of claim 1, wherein the benzene column and cumene column are operated in a way so as to satisfy Mathematical Formula 1 below:

$$T_3 - T_2 \geq 10° C. \qquad \text{[Mathematical Formula 1]}$$

wherein in the Mathematical Formula 1 above, $T_2$ is the temperature at the discharge position of the first cumene stream of the benzene column, and $T_3$ is the temperature at the discharge position of the second cumene stream of the cumene column.

6. The method of claim 1, wherein an internal pressure of the benzene column is maintained in a range of 10 kPa to 230 kPa.

7. The method of claim 1, further comprising:
    a process of passing the second polyisopropylbenzene discharged from the polyisopropylbenzene column through one or more heat exchangers selected among the heat exchanger of the benzene column and a heat exchanger of the cumene column.

* * * * *